Figure 1:
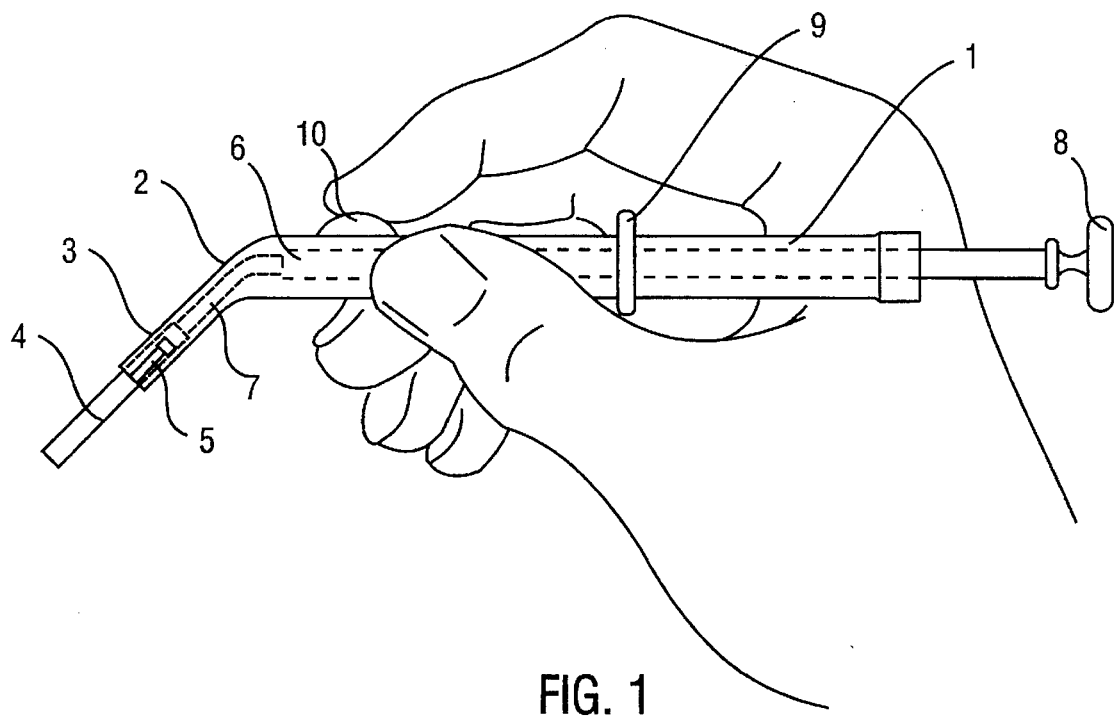

United States Patent [19]

Mühlbauer et al.

[11] Patent Number: 5,626,473
[45] Date of Patent: May 6, 1997

[54] DENTAL COMPOUND APPLICATOR

[75] Inventors: Ernst Mühlbauer; Edgar Lein, both of Hamburg, Germany

[73] Assignee: Ernst Mühlbauer KG, Hamburg, Germany

[21] Appl. No.: 560,807

[22] Filed: Nov. 21, 1995

[30] Foreign Application Priority Data

Nov. 30, 1994 [DE] Germany ................. 9419200.6

[51] Int. Cl.$^6$ ................................................ A61C 5/04
[52] U.S. Cl. .................................................... 433/89
[58] Field of Search ........................ 433/80, 89, 90, 433/96

[56] References Cited

U.S. PATENT DOCUMENTS

| | | | |
|---|---|---|---|
| 2,031,273 | 2/1936 | Marschalk | 433/89 |
| 3,028,672 | 4/1962 | Zandberg | 32/60 |
| 3,221,409 | 12/1965 | Thiel et al. | 32/60 |
| 3,792,530 | 2/1974 | Smith | 32/54 |
| 4,198,756 | 4/1980 | Dragan | 222/326 |
| 4,693,684 | 9/1987 | Blatherwick et al. | 433/90 |
| 4,726,769 | 2/1988 | Hirdes | 433/89 |
| 4,784,607 | 11/1988 | Francois | 433/89 |
| 4,805,646 | 2/1989 | Shimenkov | 433/89 |

FOREIGN PATENT DOCUMENTS

| | | | |
|---|---|---|---|
| 0237182B1 | 11/1990 | European Pat. Off. | A61C 5/06 |
| 2528116C2 | 11/1983 | Germany | A61C 5/06 |

OTHER PUBLICATIONS

European Search Report, DEU 9519200, dated Jun. 8, 1995.

*Primary Examiner*—Cary E. O'Connor
*Attorney, Agent, or Firm*—Arnold, White & Durkee

[57] ABSTRACT

A dental compound applicator, having a shaft (1) that can be gripped in pencil-hold fashion, the front end of which can be connected to a syringe (4) containing the dental compound and a plunger, and containing a piston (6) for driving forward the plunger, which piston is connected to an actuation device (10) in that region of the shaft where a fingertip is located when gripping in pencil-hold fashion. The actuation device (10) comprises a toothed wheel which is mounted on the shaft, can be rotated by the fingertip and engages in a rack provided on the piston (6). The toothed wheel can consist of a larger grip wheel to be actuated using the finger, and a smaller pinion, cooperating with the rack, so that gearing down results.

3 Claims, 2 Drawing Sheets

DENTAL COMPOUND APPLICATOR

The invention relates to a dental compound applicator, having a shaft that can be gripped in pencil-hold fashion, the front end of which is connected or can be connected to a syringe containing the dental compound and a plunger, and containing a piston for driving forward the plunger, which piston is connected to an actuation device in that region of the shaft where a fingertip is located when gripping in pencil-hold fashion.

It is known to store dental compounds, as they are used for tooth fillings, in syringe-type capsules which have a cylindrical syringe body, a plunger for ejecting the compound and a finely narrowed opening for application at the site of utilization. They are used in conjunction with applicators which have at the front end a coupling device for connection to a capsule and contain an elongated piston whose front end acts on the plunger of the capsule, and at the rear end has a thumb grip for actuation (DE-C2-25 28 116, U.S. Pat. No. 4,198,756). In particular in the case of viscous compounds, these instruments do not permit smooth emptying of the capsules. This has the result that it is difficult for the dentist to determine the amount of compound to be applied.

Instruments of the type mentioned at the outset are also known (U.S. Pat. Nos. 4,693,684, 3,221,409) in which a lever, which acts via a ratchet device on the piston equipped with a rack, is arranged at the front end of the shaft. These instruments are complicated and contain many parts, and are correspondingly expensive. In the case of a similar arrangement (EP-B 237182) the lever and the piston are formed as a single piece with a flexible intermediate part. This piston/lever is a complicated shaped piece which is susceptible to faults. In addition, the lever transmits to its piston part not only forces directed in the piston direction, but also forces directed transversely thereto, which cause a high degree of friction between the piston and the shaft, the static friction component of which, with the resulting stick-slip effect, renders accurate metering of the dental compound difficult. Finally, an instrument is known (U.S. Pat. No. 3,028,672) in which a slide that can be displaced using the fingertip is arranged at the front shaft end, which slide drives, via a rack, a series of toothed wheels which transmit the movement to a rack connected to the piston. The high number of parts in this arrangement makes it expensive. In addition, it causes a high degree of friction, which detrimentally influences the accuracy of the metering.

The object of the invention is to obtain an arrangement of the type described at the outset, which is inexpensive and permits accurate metering. The solution according to the invention consists in that the actuation device for the piston comprises a toothed wheel, mounted on the shaft, which on the one hand can be driven using the fingertip and, on the other hand, engages in a rack provided on the piston.

The actuation device for the piston therefore consists of only a single part having the simplest of shapes and functions. The instrument is therefore inexpensive to produce and not susceptible to faults during operation. The toothed wheel transmits to the piston almost exclusively forces directed in the piston direction. The degree of friction of the piston in the shaft is therefore low. The bearing friction of the toothed wheel is likewise negligibly small. Because of the low degree of friction, sticking effects which make metering of the dental compound difficult, do not occur.

According to an important feature of the invention, the toothed wheel is designed as a gear-down device, in that it has, in addition to the part cooperating with the rack, a grip wheel of larger diameter. This means that the movement of the finger is converted into a movement of the piston that is geared-down in the ratio of the diameters of the toothed wheel parts, i.e. is reduced. The grip wheel can in this case be designed in dual form, i.e. one grip wheel is provided on each side of the part of the toothed wheel that cooperates with the rack. This produces symmetrical loading of the toothed wheel, with low wear. In addition, the two grip wheels, the separation of which is slightly larger than the width of the piston or of the rack, produce the effect that the latter is securely guided laterally in the tooth-engagement region.

It is often desirable for the outlet opening of the syringe to be angled off relative to the direction of the shaft, in order to facilitate application of the dental compound. For this purpose, it is possible for the front end of the shaft to be correspondingly curved and for the piston to be flexible, which is known per se (U.S. Pat. No. 3,221,409). A lower degree of friction is achieved according to the invention in that the piston extends linearly and in that the syringe, arranged in alignment with the piston, ends in a thin, plastically bendable outlet tube which is, as required, bent into the direction desired by the dentist. This feature is worthy of protection possibly independent of the above-described features.

Figure 2:
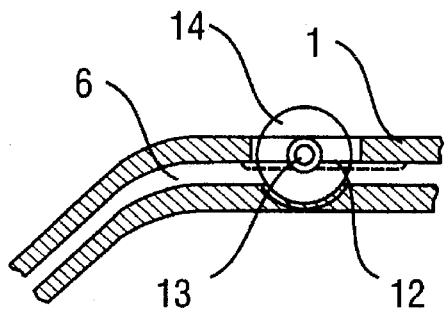
Figure 3:
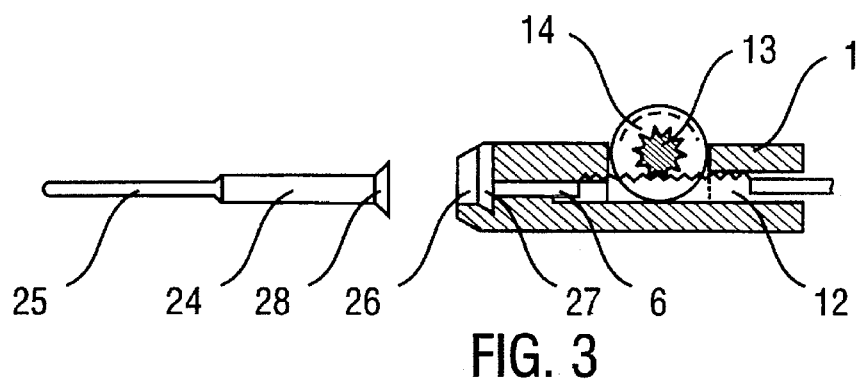
Figure 4:
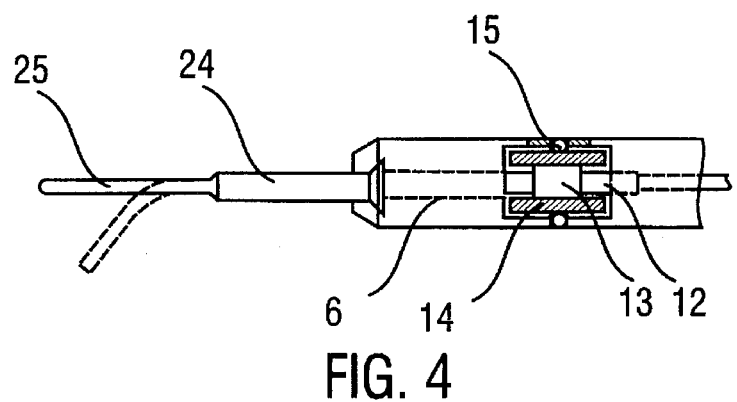
Figure 5:
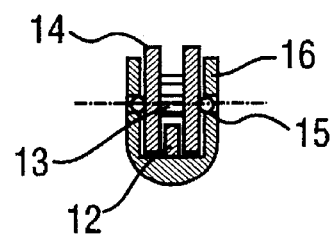

The invention is explained in more detail below with reference to the drawing which illustrates advantageous exemplary embodiments, and in which:

FIG. 1 shows an overall view of a first embodiment of the instrument in the hand of the user, FIG. 2 shows in longitudinal section the front region of the embodiment shown in FIG. 1, FIG. 3 shows the longitudinal section of the front region of a modified embodiment with associated syringe capsule in longitudinal section, FIG. 4 shows a plan view of the instrument part shown in FIG. 3, with the syringe capsule fitted, and FIG. 5 shows a cross section in the region of the toothed actuation wheel.

The instrument has an elongated shaft 1 which is, in the embodiment in FIG. 1, angled off slightly at the front end at 2 and forms at the front end a coupling device 3 for connection to a syringe capsule 4. The syringe capsule 4 is a hollow cylindrical body which contains at the rear end a plunger, in front of which the dental compound is located. The front end forms an outlet opening, which is not narrowed in the embodiment in FIG. 1, in order to provide a lower outlet resistance against a dental compound which may, if appropriate, be very viscous. During storage, the syringe capsule is closed off suitably, for example by means of a fit-on cap which is removed during use, as shown in FIG. 1.

In the example represented, the coupling device 3 is formed by a hollow cylindrical part of the shaft 1, into which the syringe capsule 4 can he tightly fitted and which has a bayonet portion 5 for cooperating with a lateral projection on the syringe capsule. Of course, it is also possible to design the coupling device in a different fashion.

The shaft 1 contains a guide bore which contains a piston 6 whose front end 7 is flexible enough for it to be able to match the curvature 2 of the shaft 1. On the rear end, projecting out of the shaft 1, of the piston 6 there is a thumb plate 8. The latter can be used, as is conventional, in conjunction with a counter-support 9 provided on the shaft 1, for pushing forward the piston 6, so that the latter acts on the plunger of the syringe capsule 4 in order to eject the dental compound therefrom.

According to the invention, an actuation device 10 which is located in the vicinity of the front end of the shaft 1 is provided additionally or instead of the thumb plate 8. This actuation device 10 is a toothed wheel which cooperates, in a manner not represented in FIG. 1, with the piston 6 in such a way that its actuation leads to forward or backward displacement of the piston 6. When the shaft 1 is held in the fashion of a pencil, as represented in FIG. 1, the toothed wheel 10 can be actuated easily by means of the index finger or thumb. Accurate positioning of the outlet opening of the syringe capsule and delicate metering can in this way be coordinated easily.

FIG. 2 shows that the piston 6 is designed as a rack at 12. This rack cooperates with the pinion 13 which is in turn connected, linked in rotation, with a grip wheel 14 which projects at the top from the shaft 1 in the region of the tip of the index finger and may be knurled, fluted or toughened on its circumference for the purpose of easier actuation. The grip wheel 14 and the pinion 13 are mounted in the shaft 1 of the instrument in a suitable manner which is not represented. The gearing down from the circumference of the grip wheel 14 to the piston 6 is preferably between 1:3 and 1:5 and in each case allows smooth forward displacement with moderate finger force. The rear end of the piston 6 can, as shown in FIG. 1, project out from the rear end of the shaft and be provided with a thumb plate 8 for easier retraction or forward displacement as far as the capsule. This is, however, not necessary.

The exemplary embodiment according to FIGS. 3 to 5 corresponds, as regards the designing of the piston 6 as a rack 12 and its cooperation with the pinion 13 and the grip wheel 14, to the exemplary embodiment just explained. FIGS. 4 and 5 show that the grip wheel 14 is designed in dual form, in that it is arranged pairwise on both sides of the pinion 13. The grip wheels 14 and the pinion 13 may be designed integrally with each other. They are at least connected together so as to be linked in rotation. They have axle stubs 15, by which they are mounted in bores that are provided in lateral walls 16 of the shaft.

The grip wheels 14 have a diameter approximately three times as large as the pinion 13. This means that movement of the finger through a particular distance corresponds to movement of the piston 6 over one third of this distance. This gearing-down leads to highly sensitive actuation of the plunger in the syringe cartridge. The syringe cartridge 24 shown in FIGS. 3 and 4 differs from that shown in FIG. 1 in that it is provided with a comparatively long and thin outlet tube 25 which (as represented in FIG. 4 by dots and dashes) can be bent easily in such a way that it retains its bent shape. This makes it possible to produce the shaft 1 of the applicator uncurved, in contrast to the embodiment according to FIG. 1, as a result of which the degree of friction between the piston and the shaft is further reduced. The external diameter of the outlet tube is, for example, in the range of from 1 to 2 mm when using a plastically deformable plastic such as polyamide.

The coupling device for connecting the applicator and the cartridge capsule 24 consists, on the shaft side, of a slot 26 whose width corresponds approximately to the diameter of the capsule cartridge 24 and of a rear segment 27 whose configuration is similar to a collar 28 at the rear end of the cartridge capsule 24. The cartridge 24 can be inserted laterally into the slot 26, 27, the dimensions being expediently selected in such a way that the syringe cartridge is temporarily fixed by frictional force in its intended position. As soon as the piston 6 has penetrated into the cartridge, as is represented in FIG. 4 with broken lines, the cartridge is secured in the coupling position. Only after the piston has been withdrawn can the coupling be again released.

We claim:

1. A dental compound applicator having a shaft that can be gripped in pencil-hold fashion, the shaft having a front end connected to a syringe containing dental compound, a plunger, and a piston for driving the plunger forward, said piston being connected to an actuation device in a region of the shaft where a fingertip is located when gripping in pencil-hold fashion, wherein the actuation device comprises a toothed wheel mounted on the shaft that can be rotated by the fingertip and engages a rack provided on the piston;

wherein the toothed wheel has, in addition to a pinion cooperating with the rack, a grip wheel of larger diameter.

2. The applicator of claim 1 wherein a grip wheel is provided on each side of the pinion.

3. The applicator of claims 1 or 2 wherein the piston extends linearly and wherein the syringe arranged in alignment with the piston, ends in a permanently bendable outlet tube.

* * * * *